US008612363B2

(12) United States Patent
Karkanias et al.

(10) Patent No.: US 8,612,363 B2
(45) Date of Patent: Dec. 17, 2013

(54) AVATAR INDIVIDUALIZED BY PHYSICAL CHARACTERISTIC

(75) Inventors: Chris Demetrios Karkanias, Sammamish, WA (US); Hubert Van Hoof, Seattle, WA (US); Kenneth D. Ray, Seattle, WA (US); Alexander G. Gounares, Kirkland, WA (US); Eric J. Horvitz, Kirkland, WA (US); Hong L. Choing, Collegeville, PA (US)

(73) Assignee: Microsoft Corporation, Redmond, WA (US)

( * ) Notice: Subject to any disclaimer, the term of this patent is extended or adjusted under 35 U.S.C. 154(b) by 866 days.

(21) Appl. No.: 12/137,677

(22) Filed: Jun. 12, 2008

(65) Prior Publication Data

US 2009/0309891 A1 Dec. 17, 2009

(51) Int. Cl.
*G06F 17/00* (2006.01)
*G06F 17/20* (2006.01)

(52) U.S. Cl.
USPC .......................................................... 706/11

(58) Field of Classification Search
None
See application file for complete search history.

(56) References Cited

U.S. PATENT DOCUMENTS

| | | | |
|---|---|---|---|
| 6,227,974 B1 * | 5/2001 | Eilat et al. ...................... 463/40 |
| 6,229,533 B1 | 5/2001 | Farmer et al. |
| 6,753,857 B1 | 6/2004 | Matsuura et al. |
| 6,817,979 B2 * | 11/2004 | Nihtila ......................... 600/300 |
| 6,910,186 B2 | 6/2005 | Kim |
| 6,957,227 B2 * | 10/2005 | Fogel et al. ........................ 1/1 |
| 7,202,816 B2 * | 4/2007 | Krumm et al. ............... 342/451 |
| 2004/0218451 A1 * | 11/2004 | Said et al. ....................... 365/222 |
| 2005/0227811 A1 * | 10/2005 | Shum et al. ....................... 482/1 |
| 2006/0089543 A1 | 4/2006 | Kim et al. |
| 2007/0074114 A1 | 3/2007 | Adjali et al. |
| 2007/0113181 A1 | 5/2007 | Blattner et al. |
| 2007/0130001 A1 * | 6/2007 | Jung et al. ....................... 705/14 |
| 2007/0158411 A1 * | 7/2007 | Krieg, Jr. ....................... 235/380 |
| 2007/0166690 A1 | 7/2007 | Johnson |
| 2007/0168226 A1 | 7/2007 | Brown |

(Continued)

FOREIGN PATENT DOCUMENTS

WO 2005074588 A2 8/2005

OTHER PUBLICATIONS

Fish'n'Steps: Encouraging physical activity with an interactive computer game': Lin, 2006, Springer-Verlag, Ubicomp LNCS, pp. 261-278.*

(Continued)

*Primary Examiner* — Kakali Chaki
*Assistant Examiner* — Peter Coughlan
(74) *Attorney, Agent, or Firm* — Lee & Hayes, PLLC (57) ABSTRACT

An avatar generator for a virtual environment reflects a physiological characteristic of the user, injecting a degree of reality into the capabilities or appearance. Thereby, many of the incentives of the real world are replicated in a virtual environment. Physiological data that reflect a degree of health of the real person can be linked to rewards of capabilities of a gaming avatar, an amount of time budgeted to play, or a visible indication. Thereby, people are encouraged to exercise. Physiological data that reflect the health and perhaps also mood also improve social interaction in virtual environments. People seeking to meet and become acquainted with particular types of people are not thwarted by the artificiality of avatars. The physiological data can be gleaned from a third party health data collection repository, a healthcare smart card, a real-time physiological sensor (e.g., blood pressure, heart rate, blood glucose, peak flow, pedometer, etc.).

42 Claims, 7 Drawing Sheets

(56) References Cited

U.S. PATENT DOCUMENTS

| | | | |
|---|---|---|---|
| 2007/0197274 A1* | 8/2007 | Dugan | 463/7 |
| 2007/0233839 A1 | 10/2007 | Gaos | |
| 2008/0082311 A1* | 4/2008 | Meijer et al. | 703/24 |

OTHER PUBLICATIONS

Vyro Games announces PIP at DEMOfal107 [online], [retrieved on May 4, 2011]. Retrieved from the Internet:<www.vyro-games.com/company/news.php.*

'Lightweight user interfaces for watch based displays': Hutterer, 2005, 6$^{th}$ Australasian User Interface Conference 2005, pp. 89-98.*

'Using games to increase exercise motivation': Yim, 2007, ACM, 978-59593-2, pp. 166-173.*

WO 2007016056 A2: Behar, 2006.*

IBM Visualization Software uses 3d Avatar to Display Human Health Records, Health and Wellbeing, http://www.gizmag.com/go/8127/. Last accessed Oct. 26, 2007, 2 pages.

Kendra Wyatt. Virtual Reality Avatars as Health Advocates, Jul. 18, 2007. http://www.changemakers.net/en-us/node/1616. 5 pages.

Rob Stein. Real Hope in a Virtual World, Online Identities Leave Limitations Behind, Oct. 6, 2007. http://www.washingtonpost.com/wp-dyn/content/article/2007/10/05/AR2007100502391.html. 4 pages.

Michael Kanellos. Under-the-skin ID Chips Move Towards U.S. Hospitals. News.com, published on ZDNet News, Jul. 27, 2004. http://news.zdnet.com/2100-9584_22-5285815.html. 12 pages.

VYRO Games. PIP—A Revolution in Stress Management. Sep. 24, 2007. www.vyro-games.com.

\* cited by examiner

AVATAR INDIVIDUALIZED BY PHYSICAL CHARACTERISTIC

BACKGROUND

Increasingly, people interact with services, information, or other people through a virtual environment. Typically, these interactions have been largely anonymous, or at least not linked to the physical individual in any way other than in self-provided identification. Often, these interactions are in a virtual space accessible by a large number of other people via a virtual persona. Examples of such virtual personas are avatars that present a sensory representation (i.e., graphical, auditory) of a particular person, often tailored to selected or predetermined characteristics. For example, a person can control an avatar as a player in a video game or as a social entity in a chat room.

This detachment of the avatar from physical limitations of the individual has often allowed exhilarating possibilities. In gaming environments, individuals are able simulate stunts and performances through their avatar that the real person could not achieve. The challenges and virtual rewards presented reinforce interest in playing. Consequently, these engrossing virtual pastimes have substantially replaced real physical exertion for many people. Unfortunately, excessive amounts of time interacting with video gaming or other virtual programming environments have negative health ramifications. This sedentary outlet provides no avenue or incentive to exercise.

The detachment of the avatar from characteristics of the individual also has many advantages in social interaction environments; individuals are able to overcome shortcomings that would otherwise inhibit them, such as pertaining to self-consciousness. However, drawbacks exist with this detachment. Others may prefer some of the cues that are available in meeting someone in person. Physical cues of a person's background, mood, socioeconomic class, ethnicity, and geographic location are readily ascertained in person. These physical characteristics assist in locating a person with aspects in common. Further, it is difficult to ascertain someone's mood, for instance, when such transient physical characteristics require the individual to self-disclose them, which may be inconvenient undesirable to provide although wanted by others. The artificiality of the avatars often results in frustration and miscommunication, thwarting the useful virtual social interaction for many people and reducing the potential for competitive interactions as well.

SUMMARY

The following presents a simplified summary of the innovation in order to provide a basic understanding of some aspects described herein. This summary is not an extensive overview of the claimed subject matter. It is intended to neither identify key or critical elements of the claimed subject matter nor delineate the scope of the subject innovation. Its sole purpose is to present some concepts of the claimed subject matter in a simplified form as a prelude to the more detailed description that is presented later.

The subject innovation relates to systems and/or methods that provide a degree of reality for how an avatar is presented or allowed to interact within a virtual space of a computing environment. Linking the avatar to a physical characteristic of a user provides leverage to provide incentives or constraints that can encourage good behavior (e.g., healthy behaviors, virtuous behaviors, etc.).

In accordance with one aspect of the subject innovation, a method is provided for interacting with a virtual environment. A physical characteristic is accessed that has been nonvolitionally obtained from a user, avoiding the inconvenience or unaccountability of voluntarily supplied information. An attribute is assigned corresponding to the physical characteristic to an avatar identified for the user. User interaction with a virtual environment can then be facilitated via the avatar as constrained by the assigned attribute.

In another aspect, a computer program product is provided for interacting with a virtual environment. A computer-readable medium has sets of codes for causing a computer to access a physical characteristic nonvolitionally obtained from a user, to assign an attribute corresponding to the physical characteristic to an avatar identified for the user, and to facilitate user interaction with a virtual environment via the avatar as constrained by the assigned attribute.

In an additional aspect, an apparatus is provided for interacting with a virtual environment. An information source is accessible for receiving a physical characteristic nonvolitionally obtained from a user. An avatar generation component assigns an attribute corresponding to the physical characteristic to an avatar identified for the user. A computing environment facilitates user interaction with a virtual environment via the avatar as constrained by the assigned attribute.

In yet a further aspect, an apparatus is provided for interacting with a virtual gaming environment. An information source is accessed for receiving a health information nonvolitionally obtained from a user. These sources are at least two of a a physiological sensor, a networked healthcare information repository, and a healthcare smart card. An avatar generation component for assigns a performance attribute corresponding to the health information characteristic to an avatar identified for the user. A computing environment facilitating user interaction with a virtual gaming environment via the avatar as constrained by the assigned performance attribute. Thereby, game players are given an incentive to improve their level of health, offsetting the otherwise disincentives of this sedentary pursuit.

The following description and the annexed drawings set forth in detail certain illustrative aspects of the claimed subject matter. These aspects are indicative, however, of but a few of the various ways in which the principles of the innovation may be employed and the claimed subject matter is intended to include all such aspects and their equivalents. Other advantages and novel features of the claimed subject matter will become apparent from the following detailed description of the innovation when considered in conjunction with the drawings.

DETAILED DESCRIPTION

An avatar generator for a virtual environment reflects a physical characteristic of the user, injecting a degree of reality into the attributes (e.g., capabilities or appearance). Thereby, many of the incentives and efficiencies of the real world are replicated in a virtual environment. Physical data that reflect a degree of health of the real person can be linked to rewards of capabilities of a gaming avatar, an amount of time budgeted to play, or a visible indication. Thereby, people are encouraged to exercise. Physical data that reflect the health, mood and other physical characteristics also improve social interaction in virtual environments. People seeking to meet and become acquainted with particular types of people are not thwarted by the artificiality of avatars. The ability to readily identify physical characteristics via an adjusted avatar can leverage the abilities of the virtual environment to go beyond what is learned in person. Hidden physical characteristics such as allergies, chronic conditions, etc., can assist in finding those who would understand someone with a like condition, or to exclude those with incompatible lifestyle limitations. The physical characteristics can be further extended to psychological traits associated with the physical person, including intelligence, religious beliefs, political affiliations, and hobbies that affect the rendering of an avatar. Providing such candid physical characteristics can be rewarded by gaining access to social virtual environments wherein such disclosure is required. The physical characteristic data can be gleaned from a third party health data collection repository, a healthcare smart card, a real-time physiological sensor (e.g., blood pressure, heart rate, blood glucose, peak flow, pedometer, etc.) to make such disclosure more convenient and verifiable.

The claimed subject matter is described with reference to the drawings, wherein like reference numerals are used to refer to like elements throughout. In the following description, for purposes of explanation, numerous specific details are set forth in order to provide a thorough understanding of the subject innovation. It may be evident, however, that the claimed subject matter may be practiced without these specific details. In other instances, well-known structures and devices are shown in block diagram form in order to facilitate describing the subject innovation.

As utilized herein, terms "component," "system," "interface," "store," "device," "network," "cloud," and the like are intended to refer to a computer-related entity, either hardware, software (e.g., in execution), and/or firmware. For example, a component can be a process running on a processor, a processor, an object, an executable, a program, a function, a library, a subroutine, and/or a computer or a combination of software and hardware. By way of illustration, both an application running on a server and the server can be a component. One or more components can reside within a process and a component can be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick, key drive . . . ). Additionally it should be appreciated that a carrier wave can be employed to carry computer-readable electronic data such as those used in transmitting and receiving electronic mail or in accessing a network such as the Internet or a local area network (LAN). Specifically, the subject innovation can be utilized with a variety of hardware configurations such as, but not limited to disability assisted input/output facilities, voice enabled input/output, tactile (e.g., Braille, etc.) keyboard, etc. Of course, those skilled in the art will recognize many modifications may be made to this configuration without departing from the scope or spirit of the claimed subject matter. Moreover, the word "exemplary" is used herein to mean serving as an example, instance, or illustration. Any aspect or design described herein as "exemplary" is not necessarily to be construed as preferred or advantageous over other aspects or designs.

Figure 1:
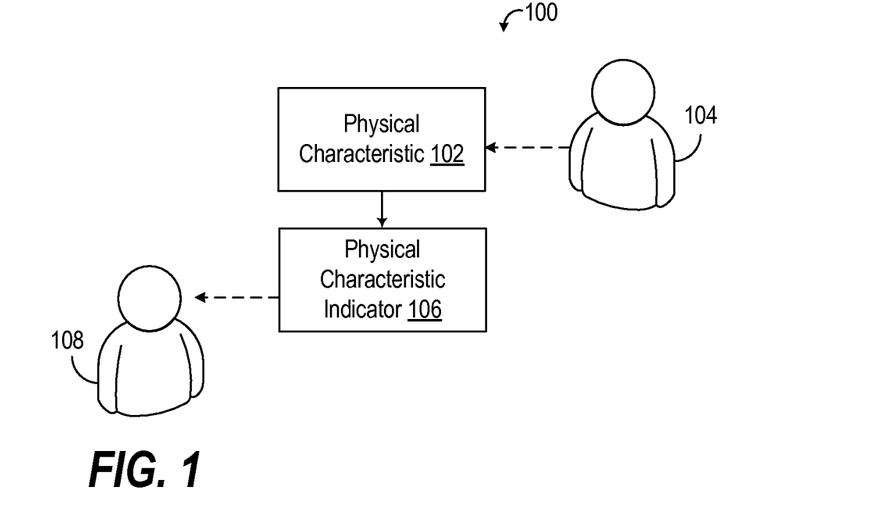
FIG. 1 illustrates a block diagram of an exemplary system that facilitates ascertaining a physical characteristic of a person for indicating to another person.

Now turning to the figures, FIG. 1 illustrates a system 100 that includes a physical characteristic capturing component 102 that facilitates ascertaining an aspect of a person 104. The physical characteristic is rendered on an indicator 106 to provide a benefit to the person 104. This benefit can reinforce positive behaviors, such as indicating a degree of health or athletic prowess, prompting further efforts by the person 104 to maintain or increase this indication. This physical characteristic can reflect a transient physical characteristic such as mood or alertness for self-awareness. Alternatively or in addition, other people 108 can benefit from additional insights into the person 104 who has a persona or avatar presented in the indicator 106.

It should be appreciated with the benefit of the present disclosure that the physical characteristics that can be conveyed include can include health information pertinent to performance such as blood pressure, heart rate, pulmonary flow rate, weight, body fat index, strength, blood glucose level. These physical characteristics can be chronic conditions such as allergies, disabilities, diseases, etc., that facilitate locating people of similar sensitivities, lifestyle and background.

In addition, the physical characteristics can include psychological and demographic information such as education level, geographic location, age, sex, intelligence quotient, socioeconomic class, occupation, marital/relationship status, religious belief, political affiliation, etc. Such information can be useful in enhancing social interaction as well as adjusting how an avatar performs in a competitive virtual environment.

Furthermore, the indicator can convey this physical characteristic to the person 104 or other people 108 in a number of fashions. For example, a virtual environment can be portable device carried by the person 104 or by other people 108, such as wirelessly informed communication device (e.g., cell phone), multimedia player device, game console, Smart Personal Object Technology (SPOT) watch, a BLUETOOTH gadget, etc.

Figure 2:
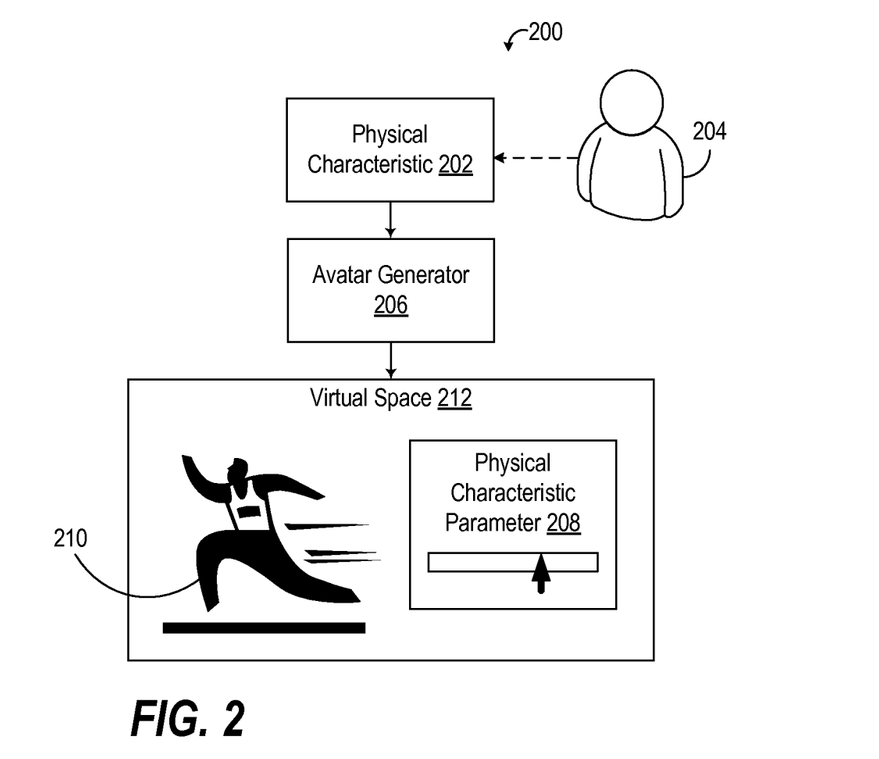
FIG. 2 illustrates a block diagram of an exemplary system that facilitates capturing a physical characteristic utilized by an avatar generator to adjust a physical characteristic of an avatar in a virtual space.

In FIG. 2, a system 200 provides self-awareness of a physical characteristic ascertained by a component 202 that provides an incentive to a person 204 to enhance the physical characteristic. An avatar generator 206 uses this physical characteristic data (e.g., health, athletic ability, skill level, etc.) to adjust a performance parameter 208 of an avatar 210 rendered in a virtual space 212. For example, a locally executed video game on a game console or other device capable of interactive play rewards players that have achieved a degree of health or athletic skill in real life, even if played in a solitary fashion. Alternatively or in addition, the degree of health can unlock additional playing time or can unlock certain aspects of a game, such as additional levels.

Figure 3:
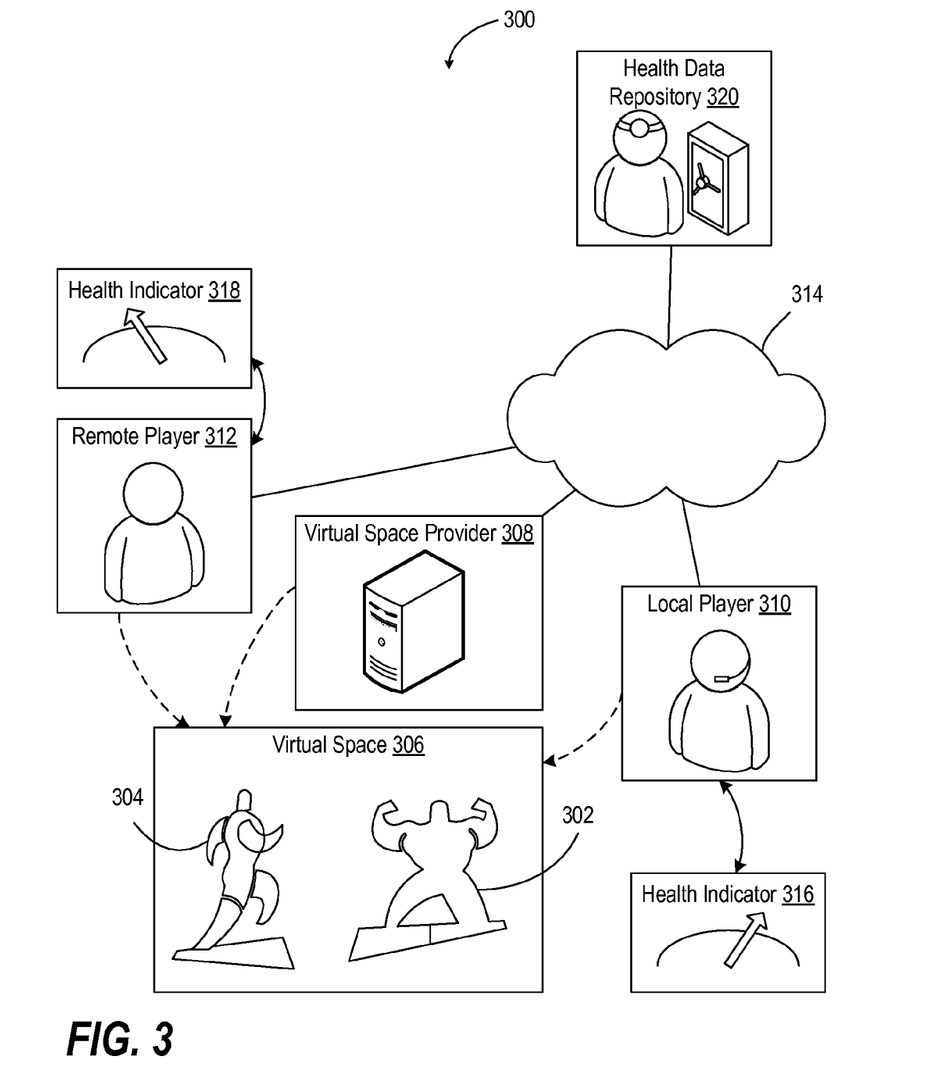
FIG. 3 illustrates a block diagram of an exemplary system that facilitates capturing a physical characteristic of health to adjust performance characteristics of a gaming avatar in gaming virtual space.

In FIG. 3, a system 300 extends features for utilizing physical characteristics (e.g., health, athletic prowess, etc.) to adjust avatars 302, 304 rendered in a virtual space 306 by a virtual space provider 308 respectively for a local player 310 and a remote player 312 over a distributed network (e.g., Internet, ad hoc network, etc.) 314. A personal characteristic for the local player 310 and the remote player 312 can be a health indicator sensor 316, 318, respectively that respond to the players 308, 310. Alternatively or in addition, physical characteristics can be derived from a trusted health data repository 320 accessible across the distributed network 310. An example of such a service is HEALTHVAULT™ by MICROSOFT® service accessible at http://www.healthvault.com.

Figure 4:
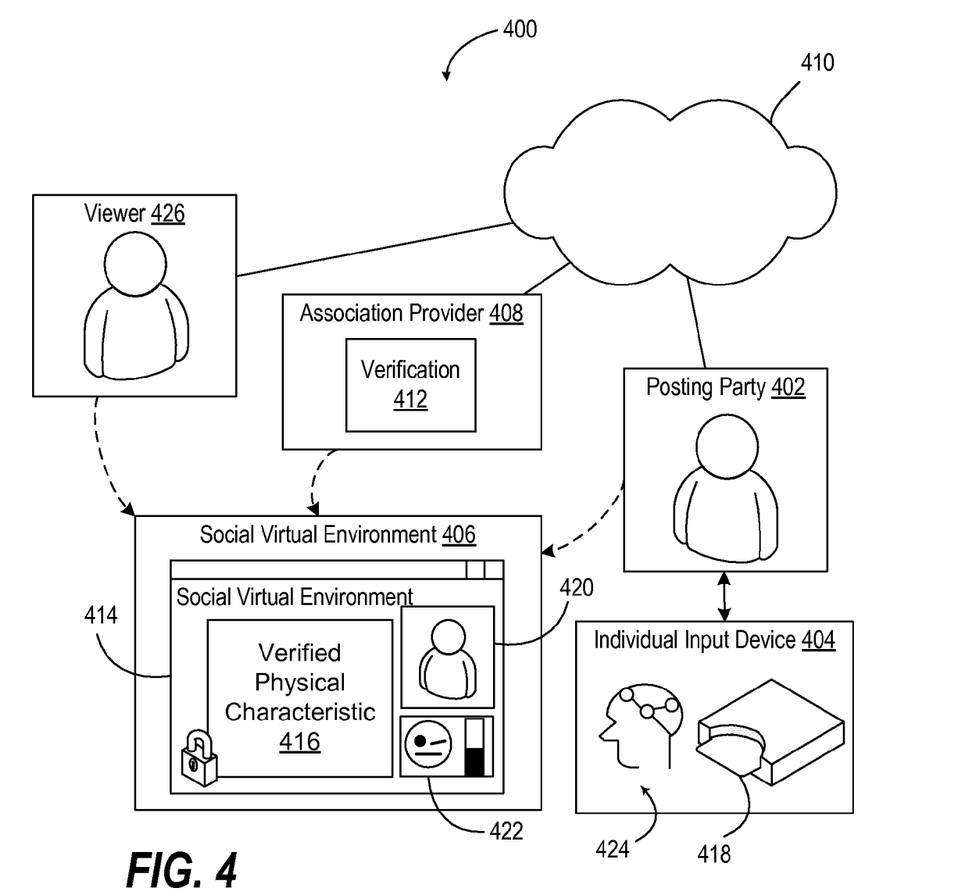
FIG. 4 illustrates a block diagram of an exemplary system that facilitates capturing a physical characteristic of a person to adjust rendering of an avatar in a social virtual environment.

In FIG. 4, a system 400 extends features for utilizing physical characteristics of a person ("posting party") 402 accessed by a verifiable individual input device 404 in a social virtual environment 406. This physical characteristic data reaches a virtual environment provider 408, such as via distributed network 410 that utilizes a verification component 412 to confirm that this data has been received in order to provide certain kinds of access to the virtual environment 406. In the exemplary depiction, a rendered avatar 414 is adjusted for this physical characteristic in a number of illustrative ways. First, a verified physical characteristic depiction 416 could be placed (e.g., a text field, an annotation on a graphic, navigation aids provided to other users, etc.) as derived from a data source (e.g., healthcare smart card reader 418). Second, a graphical rendering of an avatar 420 could have a stereotypical or custom alteration that is suggestive of the physical characteristic (e.g., size is a function of weight and height, detail variations are made as a function of age and sex, etc., attire and grooming features made stereotypical for a certain demographic of the person, etc.). Third, a time-varying graphic (e.g., cartoon, meter, etc.) 422 can reflect transient physical characteristics such as mood, alertness, interest, veracity that are detected by a physiological sensor 424.

For example, as a person utilizes Voice over IP (VoIP) to chat with a viewing person 426 in the virtual environment 406, stress could be detected to gauge honesty. As another example, skin resistance, pulse, and breathing could be detected to gauge mood. As yet another example, a webcam image or video could be verified by pattern matching to avoid spoofing. As a further example, the verification component 412 could block posting of an avatar 414 that lacks a requisite physical characteristic (e.g., left-handedness verified for a left-handed club). In addition, the viewing person 426 could interact with the avatar 414 at periods in which the person 402 is not interacting with the 406. The physical characteristics exemplified by the avatar 414 persisting for review (e.g., a profile on a dating website). The avatar 414 could incorporate sufficient intelligence so that rudimentary conversation regarding the physical characteristics could be queried.

Figure 5:
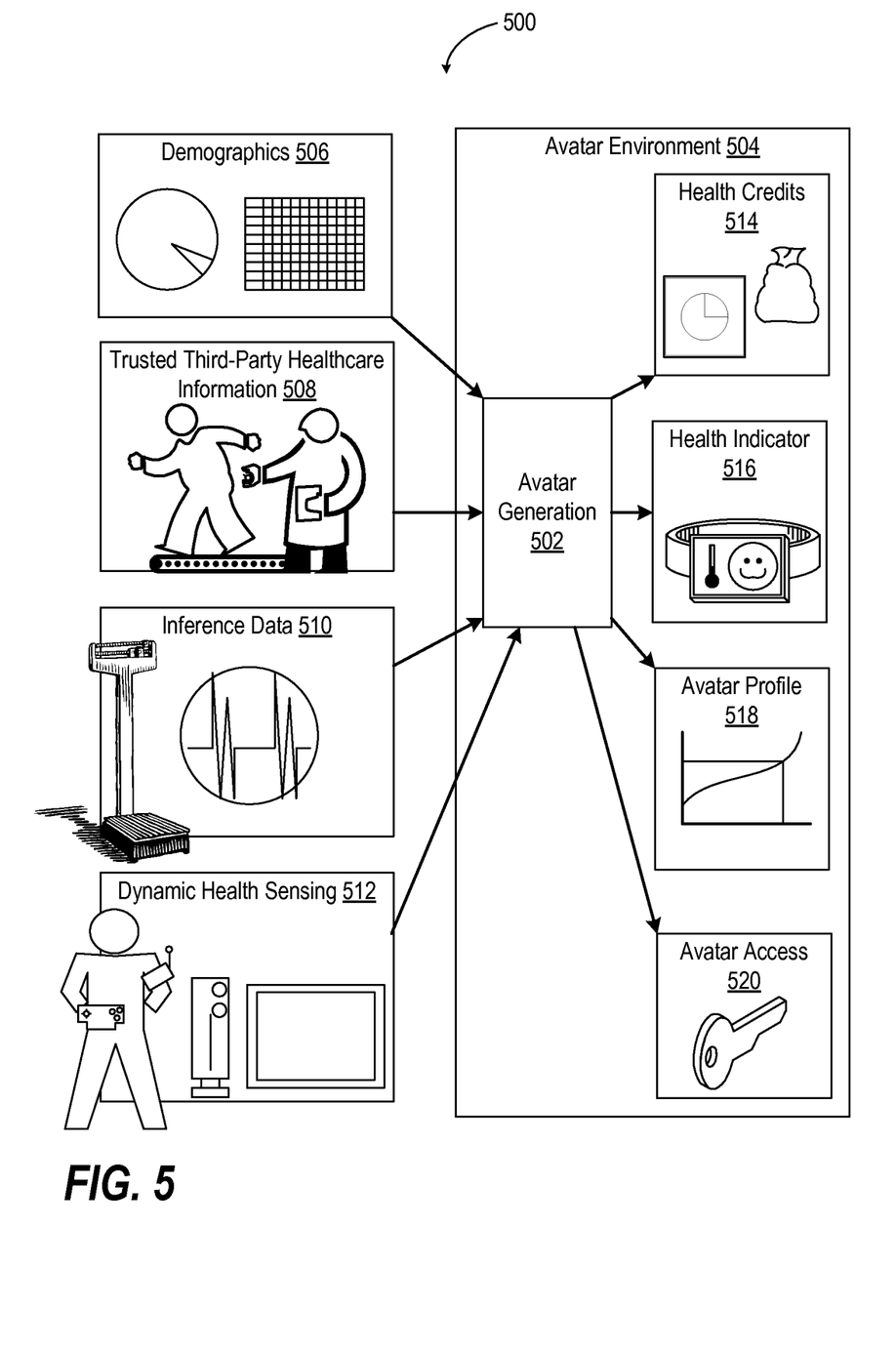
FIG. 5 illustrates a block diagram of an exemplary system that captures a plurality of sources of physical characteristic data for avatar generation that serves multiple avatar aspects that can be used by an application operating in an avatar environment.

In FIG. 5, a system 500 leverages a plurality of physical characteristic sources so that an avatar generation component 502 can direct a plurality of avatar attributes in an avatar environment 504. As one example of a physical characteristic, the avatar generation component 502 could access a demographic data component 506 for physical characteristics such as age, sex, employment experience, occupation, political affiliations, ethnicity, race, nationality, geographic home, current residence, etc. As another example, the avatar generation component 502 could access a trusted third-party healthcare information source 508 for measures of health, disease, chronic conditions, etc. As yet an additional example, the avatar generation component 502 could access inference data component 510, such as a SPOT watch previously worn during exercising that incorporates measures for a period of elevated pulse equating to exercise, miles run as detected by a pedometer, running as detected by from a location sensing system (e.g., global positioning system (GPS) device). As yet a further example, the avatar generation component 502 could access a dynamic health or mood sensing gadget 512 worn while the person interacts with the avatar environment 504.

It should be appreciated with the benefit of the present disclosure that a plurality of applications could share hosting within the avatar environment 504 that would selectively utilize portions of such avatar attributes. For example, certain applications may leverage health credits 514 earned by positive behaviors (e.g., exercising, detected honest behavior). Alternatively or in addition, an auxiliary health indicator output (e.g., BLUE TOOTH™ active mood ring, SPOT watch, etc.) 516 can communicate the physical characteristic to the user or other people.

As yet a further example, an avatar profile 518 could be assigned as a calculated measure inferred from other health/mood/demographic data. For example, a "black belt" status could be accorded a player if a certification is detected in demographic data 506, a recent clean bill of health is ascertained from third-party healthcare information 508, and the current condition of the player is rested and alert as detected from inference data 510 or dynamic health sensing 512. The player could be docked as health credits 514 erode, such as for playing too long or if the mood is sensed as becoming undesirable.

The applications in the avatar environment 504 could also utilize avatar access permissions 520 generated by the avatar generation component 502 in order to allow access to certain venues or to encourage or discourage interactions between other avatars operating with the avatar environment. For example, a game competition could enforce that only requisite health levels are allowed to compete in a certain competition level.

Figure 6:
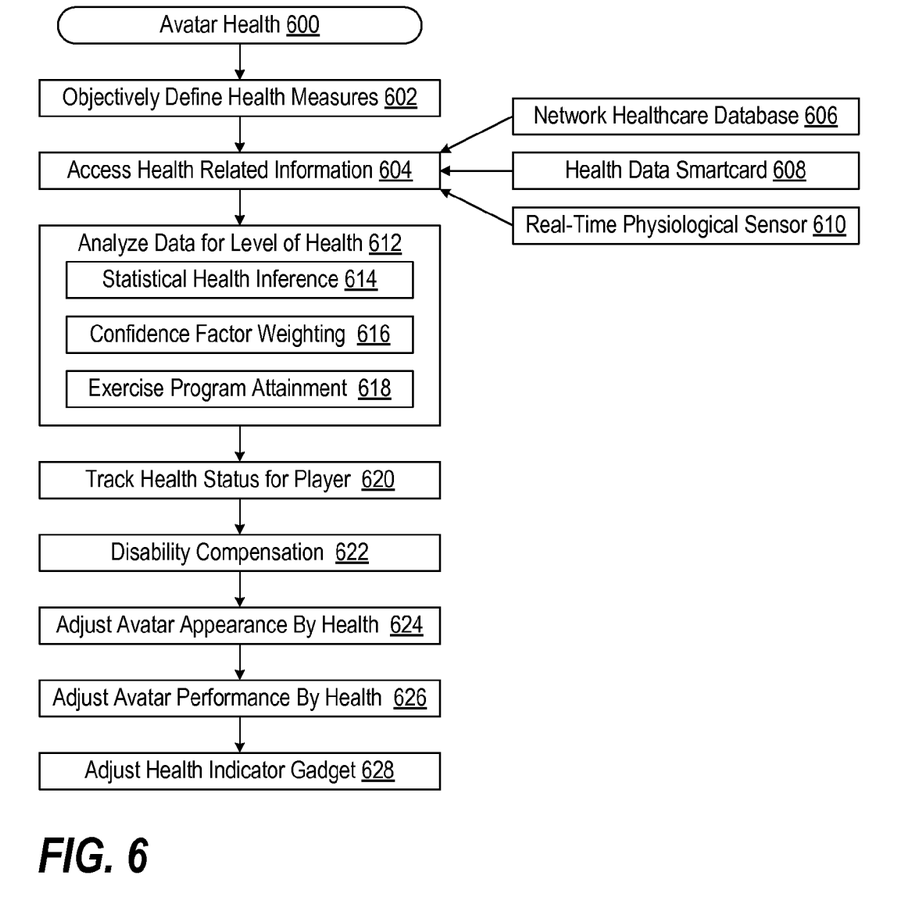
FIG. 6 illustrates a flow diagram of a methodology performed by the exemplary system to render an avatar to reflect physical characteristics ascertained about a real person.

FIG. 6 illustrates methodologies and/or flow diagrams in accordance with the claimed subject matter. For simplicity of explanation, the methodologies are depicted and described as a series of acts. It is to be understood and appreciated that the subject innovation is not limited by the acts illustrated and/or by the order of acts. For example acts can occur in various orders and/or concurrently, and with other acts not presented and described herein. Furthermore, not all illustrated acts may be required to implement the methodologies in accordance with the claimed subject matter. In addition, those skilled in the art will understand and appreciate that the methodologies could alternatively be represented as a series of interrelated states via a state diagram or events. Additionally, it should be further appreciated that the methodologies disclosed hereinafter and throughout this specification are capable of being stored on an article of manufacture to facilitate transporting and transferring such methodologies to computers. The term article of manufacture, as used herein, is intended to encompass a computer program accessible from any computer-readable device, carrier, or media.

A methodology 600 for avatar health begins in block 602 by defining an objective health measure against which persons are to be assessed. In block 604, health related information is accessed. For example, network healthcare database can be accessed as depicted at 606, a health data smart card can be accessed as depicted at 608, or a real-time physiological sensor can be accessed as depicted at block 610. The health related information is then analyzed for level of health in block 612. This determination can employ a statistic health inference as depicted in block 614. For example, a lookup table or equation can give a median health status for a person of a certain age having the accessed data (e.g., blood pressure, weight, heart rate, exercise level, etc.). Multiple sources of healthcare data can be evaluated for trustworthiness and weighted accordingly for confidence level, as depicted in block 616. For example, a physical examination that is five years ago would be weighted less than a more recent examination. A health sensor could be weighted in importance as a factor of how easily such a device could be spoofed or how tangentially the data is to indicating health. As yet another example, as depicted in block 618, the analysis of level of health could give rewards for exercise program attainment. A subjectively successful accomplishment could receive a greater reward, even if at a lower level than an average degree of health for an overall population. For example, in order to provide an on-going incentive to healthy behavior, a level of health could be gradually raised in order to give an on-going incentive. Alternatively, a disabled person could be accorded a more modest goal adjusted for the particular limitations of the disability.

In block 620, health status for a player in an avatar environment could be tracked so that future analyses and health level assignment reflect some of these considerations. Tracking could also allow extrapolation during periods in which the player is unable to provide health data. For example, the avatar environment could allow access for a period of time in which the person is in a communication environment that does not allow full communication (e.g., utilizing a limited capacity portal computing device).

In block 622, in certain implementations it can be desirable to intentionally not implement a physical characteristic in an avatar. For example, a disability can preclude certain otherwise encouraged behavior. However, in order to provide other benefits of participation such individuals could be accorded a further compensation to the attributes of their avatar.

In block 624, the avatar is adjusted in appearance to reflect the health characteristic. For example, an undesirable body weight could be reflected in an overweight or underweight appearance for the avatar. An unhealthy condition could be reflected in an unhealthy pallor, posture, etc. In block 626, the performance parameters for the avatar are adjusted to reflect health, such as speed, strength, agility, visual acuity, etc. In block 628, these measures could be replicated on a health indicator gadget, such as a SPOT watch, so that the individual or others can gauge a health level. For example, a dedicated gamer could exercise for a period of time until his health indicator gadget shows a sufficiently high health/health credit in order to allow reentering the avatar environment.

Figure 7:
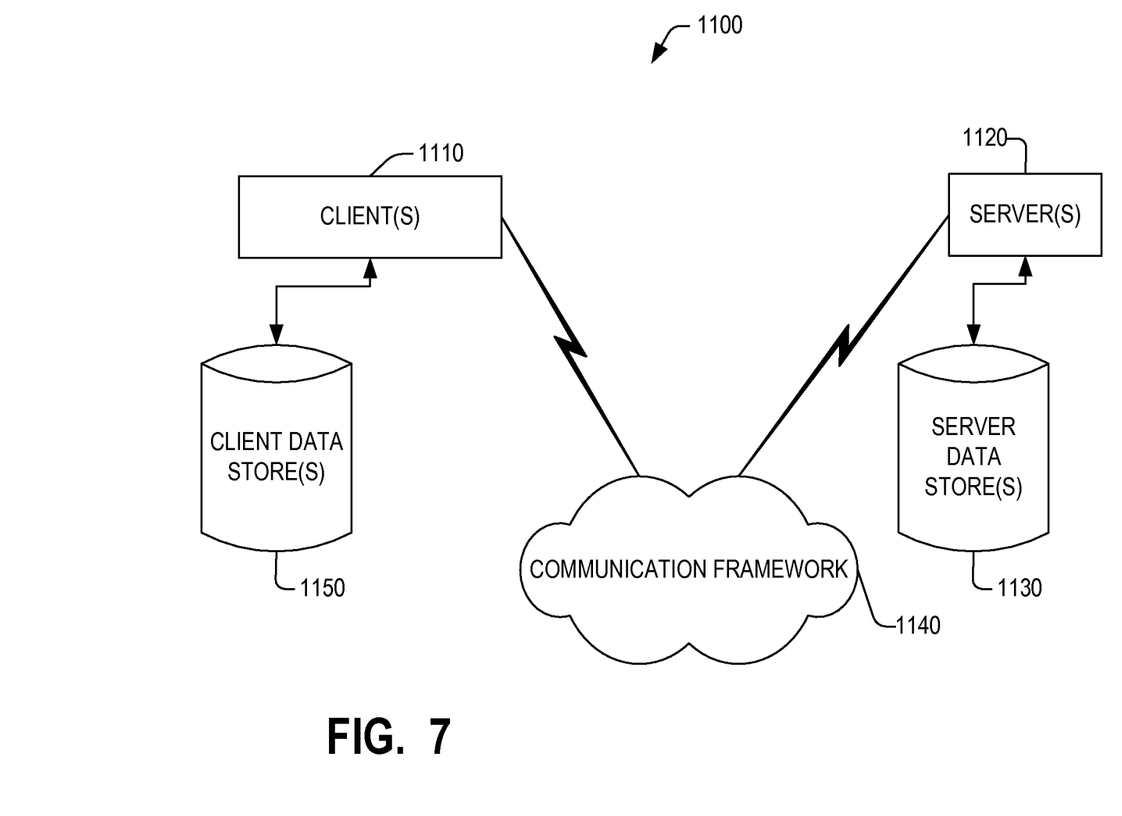
FIG. 7 illustrates an exemplary networking environment, wherein the novel aspects of the claimed subject matter can be employed.
Figure 8:
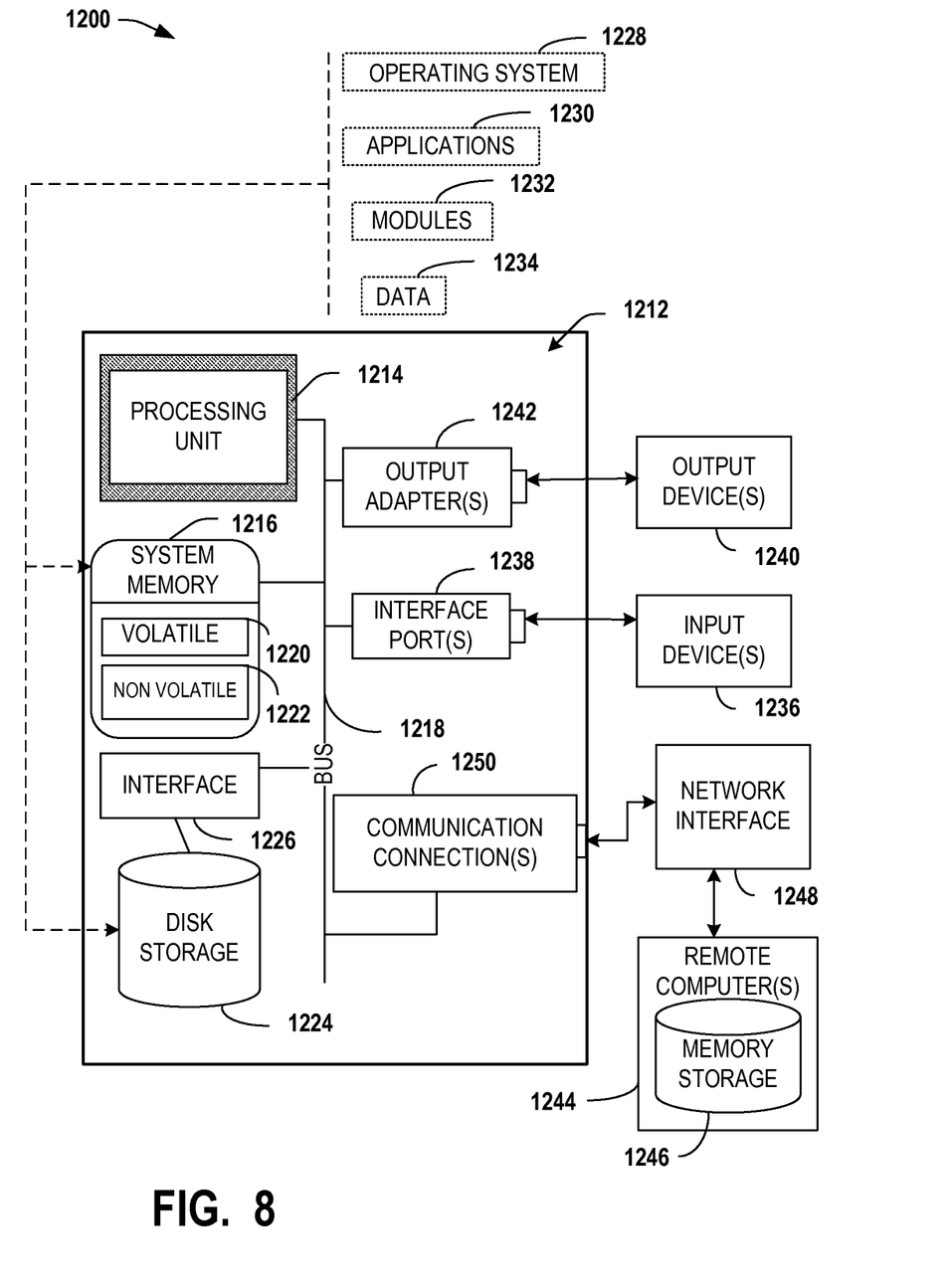
FIG. 8 illustrates an exemplary operating environment that can be employed in accordance with the claimed subject matter.

In order to provide additional context for implementing various aspects of the claimed subject matter, FIGS. 6-7 and the following discussion is intended to provide a brief, general description of a suitable computing environment in which the various aspects of the subject innovation may be implemented. For example, a counselor component that facilitates automatically generating questions to ask a doctor during an appointment, as described in the previous figures, can be implemented in such suitable computing environment. While the claimed subject matter has been described above in the general context of computer-executable instructions of a computer program that runs on a local computer and/or remote computer, those skilled in the art will recognize that the subject innovation also may be implemented in combination with other program modules. Generally, program modules include routines, programs, components, data structures, etc., that perform particular tasks and/or implement particular abstract data types.

Moreover, those skilled in the art will appreciate that the inventive methods may be practiced with other computer system configurations, including single-processor or multi-processor computer systems, minicomputers, mainframe computers, as well as personal computers, hand-held computing devices, microprocessor-based and/or programmable consumer electronics, and the like, each of which may operatively communicate with one or more associated devices. The illustrated aspects of the claimed subject matter may also be practiced in distributed computing environments where certain tasks are performed by remote processing devices that are linked through a communications network. However, some, if not all, aspects of the subject innovation may be practiced on stand-alone computers. In a distributed computing environment, program modules may be located in local and/or remote memory storage devices.

FIG. 6 is a schematic block diagram of a sample-computing environment 1100 with which the claimed subject matter can interact. The system 1100 includes one or more client(s) 1110. The client(s) 1110 can be hardware and/or software (e.g., threads, processes, computing devices). The system 1100 also includes one or more server(s) 1120. The server(s) 1120 can be hardware and/or software (e.g., threads, processes, computing devices). The servers 1120 can house threads to perform transformations by employing the subject innovation, for example.

One possible communication between a client 1110 and a server 1120 can be in the form of a data packet adapted to be transmitted between two or more computer processes. The system 1100 includes a communication framework 1140 that can be employed to facilitate communications between the client(s) 1110 and the server(s) 1120. The client(s) 1110 are operably connected to one or more client data store(s) 1150 that can be employed to store information local to the client(s) 1110. Similarly, the server(s) 1120 are operably connected to one or more server data store(s) 1130 that can be employed to store information local to the servers 1120.

With reference to FIG. 7, an exemplary environment 1200 for implementing various aspects of the claimed subject matter includes a computer 1212. The computer 1212 includes a processing unit 1214, a system memory 1216, and a system bus 1218. The system bus 1218 couples system components including, but not limited to, the system memory 1216 to the processing unit 1214. The processing unit 1214 can be any of various available processors. Dual microprocessors and other multiprocessor architectures also can be employed as the processing unit 1214.

The system bus 1218 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCM-CIA), Firewire (IEEE 1394), and Small Computer Systems Interface (SCSI).

The system memory 1216 includes volatile memory 1220 and nonvolatile memory 1222. The basic input/output system (BIOS), containing the basic routines to transfer information between elements within the computer 1212, such as during start-up, is stored in nonvolatile memory 1222. By way of illustration, and not limitation, nonvolatile memory 1222 can include read only memory (ROM), programmable ROM (PROM), electrically programmable ROM (EPROM), electrically erasable programmable ROM (EEPROM), or flash memory. Volatile memory 1220 includes random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), Rambus direct RAM (RDRAM), direct Rambus dynamic RAM (DRDRAM), and Rambus dynamic RAM (RDRAM).

Computer 1212 also includes removable/non-removable, volatile/nonvolatile computer storage media. FIG. 7 illustrates, for example, a disk storage 1224. Disk storage 1224 includes, but is not limited to, devices like a magnetic disk drive, floppy disk drive, tape drive, Jaz drive, Zip drive, LS-100 drive, flash memory card, or memory stick. In addition, disk storage 1224 can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1224 to the system bus 1218, a removable or non-removable interface is typically used such as interface 1226.

It is to be appreciated that FIG. 7 describes software that acts as an intermediary between users and the basic computer resources described in the suitable operating environment 1200. Such software includes an operating system 1228. Operating system 1228, which can be stored on disk storage 1224, acts to control and allocate resources of the computer system 1212. System applications 1230 take advantage of the management of resources by operating system 1228 through program modules 1232 and program data 1234 stored either in system memory 1216 or on disk storage 1224. It is to be appreciated that the claimed subject matter can be implemented with various operating systems or combinations of operating systems.

A user enters commands or information into the computer 1212 through input device(s) 1236. Input devices 1236 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1214 through the system bus 1218 via interface port(s) 1238. Interface port(s) 1238 include, for example, a serial port, a parallel port, a game port, and a universal serial bus (USB). Output device(s) 1240 use some of the same type of ports as input device(s) 1236. Thus, for example, a USB port may be used to provide input to computer 1212 and to output information from computer 1212 to an output device 1240. Output adapter 1242 is provided to illustrate that there are some output devices 1240 like monitors, speakers, and printers, among other output devices 1240, which require special adapters. The output adapters 1242 include, by way of illustration and not limitation, video and sound cards that provide a means of connection between the output device 1240 and the system bus 1218. It should be noted that other devices and/or systems of devices provide both input and output capabilities such as remote computer(s) 1244.

Computer 1212 can operate in a networked environment using logical connections to one or more remote computers, such as remote computer(s) 1244. The remote computer(s) 1244 can be a personal computer, a server, a router, a network PC, a workstation, a microprocessor based appliance, a peer device or other common network node and the like, and typically includes many or all of the elements described relative to computer 1212. For purposes of brevity, only a memory storage device 1246 is illustrated with remote computer(s) 1244. Remote computer(s) 1244 is logically connected to computer 1212 through a network interface 1248 and then physically connected via communication connection 1250. Network interface 1248 encompasses wire and/or wireless communication networks such as local-area networks (LAN) and wide-area networks (WAN). LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1250 refers to the hardware/software employed to connect the network interface 1248 to the bus 1218. While communication connection 1250 is shown for illustrative clarity inside computer 1212, it can also be external to computer 1212. The hardware/software necessary for connection to the network interface 1248 includes, for exemplary purposes only, internal and external technologies such as, modems including regular telephone grade modems, cable modems and DSL modems, ISDN adapters, and Ethernet cards.

What has been described above includes examples of the subject innovation. It is, of course, not possible to describe every conceivable combination of components or methodologies for purposes of describing the claimed subject matter, but one of ordinary skill in the art may recognize that many further combinations and permutations of the subject innovation are possible. Accordingly, the claimed subject matter is intended to embrace all such alterations, modifications, and variations that fall within the spirit and scope of the appended claims.

In particular and in regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the innovation includes a system as well as a computer-readable medium having computer-executable instructions for performing the acts and/or events of the various methods of the claimed subject matter.

There are multiple ways of implementing the present innovation, e.g., an appropriate API, tool kit, driver code, operating system, control, standalone or downloadable software object, etc. which enables applications and services to use the advertising techniques of the invention. The claimed subject matter contemplates the use from the standpoint of an API (or other software object), as well as from a software or hardware object that operates according to the advertising techniques in accordance with the invention. Thus, various implementations of the innovation described herein may have aspects that are wholly in hardware, partly in hardware and partly in software, as well as in software.

The aforementioned systems have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but generally known by those of skill in the art.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

What is claimed is:

1. A method, executed by a computing device, of interacting with a virtual environment, the method comprising:
   accessing physical characteristic data nonvolitionally obtained from a user, the physical characteristic data including a sensor data portion sensed from the user, a demographic data portion pertaining to a demographic of the user and a healthcare information portion pertaining to a health of the user;
   determining a trustworthiness of the healthcare information;
   analyzing the sensor data portion, the demographic data portion and the healthcare information portion;
   inferring a median health status of the user based in part on the analyzing and the trustworthiness;
   assigning an attribute corresponding to the median health status to an avatar identified for the user; and
   adjusting, by the computing device, a performance of the avatar within a virtual environment as constrained by the assigned attribute.

2. The method of claim 1, further comprising accessing, via a network, a health information repository to obtain at least a subset of the healthcare information portion.

3. The method of claim 1, further comprising accessing a health information smart card to obtain at least a subset of the healthcare information portion.

4. The method of claim 1, further comprising receiving physiological data sensed from the user, wherein the sensor data portion includes the physiological data.

5. The method of claim 4, further comprising receiving the physiological data selected from a group consisting of heart rate, flow rate, blood pressure, blood glucose level, weight, and electroencephalogram.

6. The method of claim 4, further comprising receiving exercise data for the user, wherein the sensor data portion includes the exercise data.

7. The method of claim 6, further comprising detecting a pedometer recording, wherein the exercise data includes the pedometer recording.

8. The method of claim 6, further comprising detecting the exercise data that includes an elevated heart rate over a period of time.

9. The method of claim 1, further comprising rewarding the median health status by enhancing performance of an avatar in a gaming virtual environment.

10. The method of claim 1, further comprising rewarding the median health status by increasing time allotted for interaction with a gaming virtual environment.

11. The method of claim 1, further comprising rewarding the median health status by unlocking a portion of a gaming virtual environment.

12. The method of claim 1, further comprising detecting a psychological state of the user, wherein the sensor data portion includes the physiological state.

13. The method of claim 12, further comprising detecting the psychological state selected from a group consisting of alertness, truth telling, and mood.

14. The method of claim 1, further comprising displaying the median health status on a portable indicator.

15. The method of claim 14, further comprising displaying the median health status on a Smart Personal Object Technology (SPOT) display worn by the user.

16. The method of claim 15, further comprising displaying a color indication on a display worn on a finger.

17. The method of claim 15, further comprising displaying a graphical indication on a display worn on a wrist.

18. The method of claim 1, further comprising assigning an attribute to the avatar pertaining to a demographic category of the user.

19. The method of claim 1, further comprising adjusting an assigned attribute of the avatar in compensation for a disability.

20. The method of claim 1, further comprising adjusting an assigned attribute of the avatar in compensation for a subjectively successful goal attainment associated with the median health status.

21. One or more computer-readable hardware storage devices storing computer-executable instructions that, upon execution by one or more processors, configure the one or more processors to perform acts comprising:
   accessing physical characteristic data nonvolitionally obtained from a user, the physical characteristic data including health information pertaining to the user, the health information including a portion obtained from multiple information repositories accessible over a network;
   determining a trustworthiness of the health information;
   determining a, degree of health of the user based In part on the trustworthiness of the health information: and
   assigning an attribute corresponding to the degree of health to an avatar identified for the user, a performance of the avatar being adjusted based in part on the degree of health; and providing user interaction with a virtual environment via the avatar as constrained by the assigned attribute.

22. An apparatus for interacting with a virtual environment, the apparatus comprising:

memory;

one or more processors communicatively coupled to the memory;

modules stored on the memory and executed by the one or more processors, the modules configured to:

receive physical characteristic data nonvolitionally obtained from a user from an information source, the physical characteristic data including a healthcare information portion, wherein the healthcare information portion includes healthcare data obtained from multiple information repositories accessible over a network;

determine a trustworthiness of the healthcare data obtained from the multiple information repositories;

analyze the physical characteristic data; and infer a level of health of the user based at least in part on the analysis of the physical characteristic data and the determined trustworthiness;

assign an attribute corresponding to the level of health to an avatar identified for the user; and adjust user interaction with a virtual environment via the avatar as constrained by the assigned attribute.

23. The apparatus of claim 22, wherein the information source comprises a health information source.

24. The apparatus of claim 22, the modules further configured to obtain at least a subset of the healthcare information portion from a health information smart card.

25. The apparatus of claim 22, the modules further configured to obtain at least a subset of the physical characteristic data from a physiological sensor responsive to the user.

26. The apparatus of claim 25, wherein the physiological sensor senses physiological data selected from a group consisting of heart rate, flow rate, blood pressure, blood glucose level, weight, and electroencephalogram.

27. The apparatus of claim 25, the modules further configured to obtain at least a subset of the physical characteristic data from an exercise data sensor.

28. The apparatus of claim 27, wherein the exercise data sensor is configured to sense a pedometer recording.

29. The apparatus of claim 27, wherein the exercise data sensor is configured to sense an elevated heart rate over a period of time.

30. The apparatus of claim 22, the modules further configured to reward the level of health by enhancing performance of an avatar in a gaming virtual environment.

31. The apparatus of claim 22, the modules further configured to reward the level of health by increasing time allotted for interaction with a gaming virtual environment.

32. The apparatus of claim 22, the modules further configured to reward the level of health by unlocking a portion of a gaming virtual environment.

33. The apparatus of claim 22, the modules further configured to obtain a psychological state of the user from a psychological sensor, wherein the physical characteristic data includes the psychological state.

34. The apparatus of claim 33, wherein the psychological sensor is responsive to the psychological state selected from a group consisting of alertness, truth telling, and mood.

35. The apparatus of claim 22, the modules further configured to display the level of health on a portable indicator.

36. The apparatus of claim 35, the modules further configured to display the level of health on a Smart Personal Object Technology (SPOT) display worn by the user.

37. The apparatus of claim 36, the modules further configured to display a color indication corresponding to the level of health on a display worn on a finger.

38. The apparatus of claim 36, the modules further configured to graphically depict the level of health on a display worn on a wrist.

39. The apparatus of claim 22, wherein the physical characteristic data includes a demographic category of the user.

40. The apparatus of claim 22, the modules further configured to adjust an assigned attribute of the avatar in compensation for a disability.

41. The apparatus of claim 22, the modules further configured to adjust an assigned attribute of the avatar in compensation for a subjectively successful goal attainment associated with the level of health.

42. An apparatus for interacting with a virtual gaming environment, the apparatus comprising:

memory;

one or more processors communicatively coupled to the memory;

modules stored on the memory and executed by the one or more processors, the modules configured to:

receive health information nonvolitionally obtained from a user, the information sources including a physiological sensor that provides physiological information, a networked healthcare information repository that provides healthcare information, and a demographic data component that provides demographic information;

determine a trustworthiness of the healthcare information obtained from the healthcare information repository;

analyze the physiological information, the healthcare information and the demographic information;

infer a median health status of the user based in part on the analysis of the physiological information and the determined trustworthiness;

assign a performance attribute corresponding to the median health status to an avatar identified for the user; and provide user interaction with a virtual gaming environment via the avatar as constrained by the assigned performance attribute.

* * * * *